United States Patent
Prathap et al.

(10) Patent No.: US 11,058,682 B2
(45) Date of Patent: Jul. 13, 2021

(54) GASTRO-RESISTANT FORMULATION CONTAINING POSACONAZOLE

(71) Applicant: ALFRED E. TIEFENBACHER (GMBH & CO. KG), Hamburg (DE)

(72) Inventors: Vamshi Ramana Prathap, Karimnagar (IN); Venkatasimhadri Naidu Kalamata, Kukatpally Hyderabad (IN); Bala Ramesha Chary Rallabandi, Bachupally Hyderabad (IN); Vinay Kumar Katakam, Khammam (IN); Hendrik Schlehahn, Travebrück (DE)

(73) Assignee: ALFRED E. TIEFENBACHER (GMBH & CO. KG), Hamburg (DE)

( * ) Notice: Subject to any disclaimer, the term of this patent is extended or adjusted under 35 U.S.C. 154(b) by 70 days.

(21) Appl. No.: 15/751,010

(22) PCT Filed: Jul. 21, 2016

(86) PCT No.: PCT/EP2016/067469
§ 371 (c)(1),
(2) Date: Feb. 7, 2018

(87) PCT Pub. No.: WO2017/025292
PCT Pub. Date: Feb. 16, 2017

(65) Prior Publication Data
US 2018/0228798 A1    Aug. 16, 2018

(30) Foreign Application Priority Data

Aug. 8, 2015 (IN) .......................... 2440/DEL/2015
Feb. 26, 2016 (IN) .......................... 201611006795
Feb. 26, 2016 (IN) .......................... 201611006796

(51) Int. Cl.
*A61K 31/496* (2006.01)
*A61K 9/16* (2006.01)
*A61K 9/20* (2006.01)
*A61K 9/28* (2006.01)

(52) U.S. Cl.
CPC .......... *A61K 31/496* (2013.01); *A61K 9/1611* (2013.01); *A61K 9/1617* (2013.01); *A61K 9/1623* (2013.01); *A61K 9/1635* (2013.01); *A61K 9/1641* (2013.01); *A61K 9/1652* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/284* (2013.01)

(58) Field of Classification Search
None
See application file for complete search history.

(56) References Cited

U.S. PATENT DOCUMENTS

| | | | |
|---|---|---|---|
| 2001/0038852 A1* | 11/2001 | Kolter | A61K 9/2027 424/465 |
| 2007/0178152 A1* | 8/2007 | Shelton | A61K 9/10 424/464 |
| 2008/0193543 A1* | 8/2008 | Morello, III | A61K 9/0004 424/490 |
| 2009/0136555 A1* | 5/2009 | Crowley | A61K 9/006 424/422 |
| 2011/0034478 A1* | 2/2011 | Fang | A61K 9/1652 514/254.07 |
| 2011/0123627 A1* | 5/2011 | Fang | A61K 31/496 424/489 |
| 2015/0231081 A1 | 8/2015 | Kulkarni et al. | |
| 2017/0027931 A1 | 2/2017 | Wan et al. | |

FOREIGN PATENT DOCUMENTS

| | | | |
|---|---|---|---|
| CN | 104510707 A | 4/2015 | |
| CN | 104546724 A | 4/2015 | |
| CN | 104721141 A | 6/2015 | |
| WO | WO 2009/088959 A1 | 7/2009 | |
| WO | WO-2010026467 A2 * | 3/2010 | A61K 31/4015 |
| WO | WO 2014/081581 A2 | 5/2014 | |
| WO | WO 2015/154718 A1 | 10/2015 | |

OTHER PUBLICATIONS

European Pharmacopoeia, 8th Ed., vol. 1 (2013), p. 288-295 & 779. (Year: 2013).*
European Examination Report issued in corresponding European Patent Application No. 16 741 934.0 dated Sep. 5, 2018.
BASF, Pharma Ingredients & Services, "Technical information about Kollicoat MAE grades", Nov. 2010, pp. 1-12.
International Search Report, issued in PCT/EP2016/067469, dated Oct. 12, 2016.
Prescribing Label of Noxafil delayed release tablets, dated Nov. 25, 2013, 32 pages total.
Written Opinion of the International Searching Authority, issued in PCT/EP2016/067469, dated Oct. 12, 2016.
Extended European Search Report, dated Nov. 14, 2019, for European Application No. 19000308.7.

* cited by examiner

*Primary Examiner* — Dominic Lazaro
(74) *Attorney, Agent, or Firm* — Birch, Stewart, Kolasch & Birch, LLP

(57) ABSTRACT

The present invention relates to a gastro-resistant pharmaceutical composition comprising a solid solution prepared by hot-melt extrusion, whereby the solid solution contains posaconazole, an enteric polymer and a non-enteric polymer. The composition is preferably a granulate material that can be filled into a capsule or compressed into a tablet.

21 Claims, No Drawings

GASTRO-RESISTANT FORMULATION CONTAINING POSACONAZOLE

The present invention relates to a gastro-resistant pharmaceutical composition comprising posaconazole.

Posaconazole is a triazole antifungal drug marketed under the tradename Noxafil® as a solution for injection, oral suspension and gastro-resistant tablet for the treatment and prophylaxis of invasive fungal infections. Noxafil® is in particular indicated for the prophylaxis of invasive *Aspergillus* and *Candida* infections in severely immunocompromised patients, such as hematopoietic stem cell transplant recipients with a graft-versus-host-disease and patients with hematologic malignancies with prolonged neutropenia from chemotherapy. The oral suspension is indicated for the treatment of oropharyngeal candidiasis.

Posaconazole is a white powder with a low aqueous solubility, whereby posaconazole's bioavailability in the oral suspension is significantly enhanced when coadministered with food. For this reason, the oral suspension should be administered during or immediately following a full meal to enhance the oral absorption of the drug. The gastro-resistant tablet has an improved bioavailability and can be administered without regard to food.

It is commonly known that the dissolution behavior of a drug depends on its solid state. Different crystalline forms of a drug usually exhibit different dissolution profiles, whereby amorphous forms are generally much more soluble than their crystalline counterparts. In addition, the chemical and physical stability of a drug are dependent on the solid state. Quite often, metastable crystalline or amorphous forms of a drug have to be stabilized in the pharmaceutical composition in order to prevent chemical degradation and interconversion of the crystalline forms/recrystallization of the amorphous form and, thus, fluctuations in the bioavailability.

WO 99/18097 discloses the crystalline forms I, II and III of posaconazole. Form I is the most stable form that does not convert into any other crystalline form under normal storage conditions or under specific stress conditions. The crystalline forms II and III convert into the form I at temperatures between 100 and 125° C.

WO 2009/147075 discloses the crystalline form Y of posaconazole. The form Y is as stable as form I but has a better water solubility, which results in an improved bioavailability.

WO 2010/000668 reports that the crystalline form IV of posaconazole has a better stability in an aqueous suspension and a better water solubility as form I due to a smaller particle size and, thus, larger specific surface area. The crystalline form IV can be directly used for a pharmaceutical composition, i.e. without the need of reducing the particle size by micronization.

WO 2011/158248 discloses the crystalline form V of posaconazole, while WO 2011/003992 discloses the crystalline form II-S from which the other crystalline forms, in particular the crystalline form IV may be obtained.

As an alternative approach for overcoming the solubility problems encountered with posaconazole, WO 98/00113 suggests a pharmaceutical composition comprising a solid solution of the drug within a polymer. The solid solution is prepared by dissolving the drug and a soluble polymer in a suitable organic solvent, followed by removing the solvent, or by dissolving the drug in a suitable organic solvent and adding an insoluble polymer, followed by absorbing the solution into the insoluble polymeric matrix. Preferably, the polymer is povidone or crospovidone.

WO 2009/129301 discloses a solid solution of posaconazole within hydroxypropyl methylcellulose acetate succinate (HPMCAS) by spray-drying a solution containing the drug and the polymer. It is further suggested that the solid solutions may be prepared by using hot-melt extrusion.

WO 2009/129300 discloses the preparation of a solid solution containing posaconazole within a hydroxypropyl methylcellulose derivative, preferably HPMCAS. It has been found that posaconazole forms a solution with the polymer behaving as a eutectic having a melting point below the melting point of the drug (about 169° C.). Hence, the use of hydroxypropyl methylcellulose derivatives for the preparation of the solid solution minimizes thermal decomposition and oxidation of posaconazole during the preparation compared to processes which utilize higher melting polymers. WO 2009/129300 further suggests that the solid solution may additionally contain a plasticizer and an antioxidant.

In view of the above described state of the art, the objective underlying the present invention was the provision of a pharmaceutical composition, in which posaconazole is physically and chemically stable. This objective is attained by the subject matter as defined in the claims.

The pharmaceutical composition of the present invention is a gastro-resistant pharmaceutical composition. Gastro-resistant formulations are designed to release the drug in the intestines. According to the European Pharmacopoeia 8.0, gastro-resistant dosage forms are delayed-release dosage forms that are intended to resist the gastric fluid and to release their drug(s) in the intestinal fluid. The gastro-resistance minimizes the food effect of the pharmaceutical composition of the present invention and, thus, improves the bioavailability of the drug. The gastro-resistant pharmaceutical composition of the present invention comprises posaconazole molecularly dispersed in a mixture containing an enteric polymer and a non-enteric polymer, wherein the mixture is prepared by hot-melt extrusion.

The enteric polymer is preferably selected from hypromellose derivatives, cellulose derivatives, polyvinylacetate derivatives and polymethacrylic acid derivatives. Examples of hypromellose derivatives include hydroxypropyl methylcellulose phthalate (HPMCP, e.g. available as HP-50 or HP-55 from Shin-Etsu Chemical Co., Ltd. Japan), hydroxypropyl methylcellulose succinate and hydroxypropyl methylcellulose acetate succinate (HPMCAS, e.g. available as AQOAT® from Shin-Etsu Chemical Co., Ltd. Japan). An example of a polyvinylacetate derivative is polyvinylacetate phthalate (PVAP), while examples of cellulose derivatives include cellulose acetate phthalate (CAP), cellulose acetate terephthalate, cellulose acetate isophthalate, cellulose acetate butyrate (CAB), cellulose acetate trimellitate (CAT), methylcellulose acetate phthalate and hydroxypropylcellulose acetate phthalate. Examples of polymethacrylic acid derivatives include poly(methacrylic acid/methyl methacrylate) 1:1 (e.g. available as Eudragit® L 100 from Evonik, Germany), poly(methacrylic acid/methyl methacrylate) 1:2 (e.g. available as Eudragit® S 100 from Evonik, Germany) and poly(methacrylic acid/ethyl acrylate) (e.g. available as Kollicoat® MAE from BASF SE, Germany). According to a preferred embodiment of the present invention, the enteric polymer is a polymethacrylic acid derivative selected from poly(methacrylic acid/methyl methacrylate) and poly(methacrylic acid/ethyl acrylate).

The pharmaceutical composition of the present invention contains a non-enteric polymer that is preferably selected from polyvinylpyrrolidone (povidone), poly(vinylpyrrolidone/vinylacetate) (copovidone), polyvinylcaprolactam/ polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyacrylates, polymethacrylates, vinylacetate polymers such as copolymers of vinyl acetate and crotonic acid, polyvinyl alcohol, partially saponified polyvinylalcohol, macrogolglycerol hydroxystearate, polyethylene glycol, hypromellose, hydroxypropyl cellulose, hydroxyethyl cellulose and maltodextrins.

According to a preferred embodiment of the present invention, the pharmaceutical composition contains an antioxidant. Preferably, the antioxidant is contained in the mixture comprising posaconazole, the enteric polymer and the non-enteric polymer. Examples of antioxidants include butylated hydroxytoluene (BHT), butylated hydroxyanisole (BHA), sodium or potassium metabisulfite, sodium bisulfite, sodium sulfite, sodium thiosulfate, cysteine, acetyl cysteine, methionine, glutathione, sodium formaldehyde sulfoxylate, ascorbic acid and its derivatives like sodium ascorbate, ascorbyl palmitate, tocopherol and its derivatives, tocopheryl succinate, tocopheryl polyethylene glycol succinate (TPGS), and propyl gallate. Preferably, the antioxidant is propyl gallate. Typically, the antioxidant is present in the composition in an amount of 0.001-2 wt.-%, preferably 0.01-1 wt.-%. Optionally the pharmaceutical composition of the present invention contains in addition an antioxidant synergist, e.g. citric acid, tartaric acid, or ethylenediaminetetra acetic acid (EDTA).

The mixture contained in the composition of the present invention may additionally contain a monomeric plasticizer, e.g. triethyl citrate, triacetin, dibutyl sebacate, diethyl phthalate, glycerylmonostearate, glycerine and propylene glycol.

Posaconazole has a melting point of 170-172° C., but it degrades at temperatures above 160° C. Hence, the hot-melt extrusion used for the preparation of the gastroresistant pharmaceutical composition of the present invention has to be conducted at temperatures below 160° C. Preferably, the hot-melt extrusion is conducted at a temperature of 40-160° C., more preferred at a temperature of 120-150° C. The hot-melt extrusion has to be carried out at a temperature that allows the dissolution of the posaconazole used as staring material within the mixture of the enteric polymer and the non-enteric polymer. In principle, any crystalline form of posaconazole as well as the amorphous form may be used for the preparation of the gastro-resistant pharmaceutical composition of the present invention.

The temperature of the hot-melt extrusion can be decreased when using a mixture of an enteric polymer and a non-enteric polymer, so that it is possible to process polymers with relatively high glass transitions temperatures. In addition, the non-enteric polymer, in particular polyvinylpyrrolidone, poly(vinylpyrrolidone/vinylacetate) and polyvinylcaprolactam/polyvinylacetate/polyethylene glycol graft copolymer, may serve as a solubility enhancer for posaconazole and may avoid recrystallization of the drug during dissolution in the intestines. Moreover, since the hot-melt extrusion works at relatively low temperatures, it is possible to use relatively volatile antioxidants as BHA and BHT as well as antioxidants, which degrade at processing temperatures above 140° C., e.g. sodium metabisulfite.

Typically, the extrudate contains the enteric polymer and the non-enteric polymer in a weight ratio of 6:1 to 1:1, preferably of 4:1 to 2:1 and more preferred of 3:1 to 2.5:1. Furthermore, the weight ratio of posaconazole to total polymer content of the extrudate is from 1:1 to 1:5, preferably from 1:2 to 1:4, and more preferred 1:2 to 1:2.5. According to a preferred embodiment of the present invention the enteric polymer is poly(methacrylic acid/ethyl acrylate) and the non-enteric polymer is selected from poly(vinylpyrrolidone/vinylacetate), polyethylene glycol, hydroxypropyl cellulose and polyvinylpyrrolidone.

It has been found that the presence of a sugar alcohol in the mixture that is subjected to hot-melt extrusion may increase the chemical stability of posaconazole and also the processability, in particular, if an acidic polymer as poly (methacrylic acid/ethyl acrylate) is present. Preferred sugar alcohols are xylitol, sorbitol, mannitol, maltitol, isomalt, lactitol and erythritol.

The pharmaceutical composition of the present invention is preferably a granulate material, whereby the granules may be coated with an enteric polymer. It is preferred that the enteric coating of the granules and the enteric polymer constituent of the granules comprise the same enteric polymer. According to a preferred embodiment, the granules consist of posaconazole, an enteric polymer, a non-enteric polymer and, optionally, an antioxidant, a sugar alcohol and/or a plasticizer.

The granules may be filled into a capsule or compressed into a tablet. The tablet, which is prepared by compressing the optionally enteric-coated granules of the present invention, may be coated with an enteric polymer or an immediate-release coating, too.

The capsule or tablet of the present invention may contain additional pharmaceutical excipients as extragranular component, e.g. diluents, binders, disintegrants, glidants and lubricants. Examples of diluents include microcrystalline cellulose, calcium hydrogen phosphate, lactose (anhydrous or monohydrate), and calcium carbonate. As binders may be used methyl cellulose, hydroxypropyl methylcellulose (HPMC), hydroxypropyl cellulose (HPC), pregelatinized starch, povidone and copovidone. Examples of disintegrants include croscarmellose sodium, sodium starch glycolate, polyvinylpolypyrrolidone (crospovidone) and low-substituted hydroxypropyl cellulose (L-HPC). As glidants silicone dioxide, talk and the like may be used, while magnesium stearate, calcium stearate, stearic acid, sodium stearyl fumarate and glycerol dibehenate are examples of suitable lubricants.

The following examples are intended to further illustrate the present invention.

EXAMPLES

Hot melt extrusion was performed with a Pharma 11 Twin-screw hot melt extruder from Thermo Fisher Scientific Inc. The used film coating system Opadry II® 85F520152 yellow comprises polyvinyl alcohol, titanium dioxide, polyethylene glycol/macrogol, talc and yellow iron oxide.

Example 1

| Ingredients | mg |
| --- | --- |
| Stage-A: (Hot-melt extrusion) | |
| Posaconazole (Form I) | 100 |
| Methacrylic acid/ethyl acrylate copolymer (1:1), Type B (Kollicoat ® MAE 100P) | 150 |
| Polyethylene glycol 1450 (Macrogol 1450) | 30 |
| Copovidone (Kollidon ® VA 64) | 25 |
| Sorbitol (Neosorb ® P 100 T) | 20 |
| Total weight after HME | 325 |

-continued

| Ingredients | mg |
|---|---|
| Stage-B: (Blending and Lubrication) | |
| Posaconazole HME granules | 325 |
| Low-substituted Hydroxypropylcellulose (L-HPC LH-11) | 60 |
| Microcrystalline cellulose (Comprecel ® M 102D+) | 165 |
| Colloidal silicon dioxide (Aerosil ® 200 pharma) | 4 |
| Croscarmellose sodium | 42 |
| Sodium stearyl fumarate (Pruv ®) | 4 |
| Core tablet weight | 600 |
| Stage-C: (Coating) | |
| Opadry II ® 85F520152 yellow | 18 |
| Water, purified | q.s. |
| Coated tablet weight | 618 |

Process:

Posaconazole and the excipients of stage A were sifted and blended. The mixture was subjected to hot melt extrusion and the obtained extrudate was milled. Low-substituted hydroxypropylcellulose, microcrystalline cellulose, silicon dioxide, croscarmellose sodium, and sodium stearyl fumarate were sifted and blended with the extrudate. The mixture was subjected to compression to obtain a tablet, which was finally film-coated.

Example 2

| Ingredients | mg |
|---|---|
| Stage-A: (Hot-melt extrusion) | |
| Posaconazole (Form I) | 100 |
| Methacrylic acid/ethyl acrylate copolymer (1:1), Type B (Kollicoat ® MAE 100P) | 150 |
| Polyethylene glycol 1450 (Macrogol 1450) | 30 |
| Copovidone (Kollidon ® VA 64) | 25 |
| Sorbitol (Neosorb ® P 100 T) | 20 |
| Total weight after HME | 325 |
| Stage-B: (Enteric coating by top-spray granulation) | |
| Kollicoat MAE 100P | 10 |
| Polyethylene glycol 400 | 2 |
| Water, purified | q.s |
| Total weight of granules | 337 |
| Stage-C: (Blending and Lubrication) | |
| Posaconazole HME granules | 337 |
| Low-substituted Hydroxypropylcellulose (L-HPC 11) | 60 |
| Microcrystalline cellulose (Comprecel M 102D+) | 153 |
| Colloidal silicon dioxide (Aerosil 200 pharma) | 4 |
| Croscarmellose sodium | 42 |
| Sodium stearyl fumarate | 4 |
| Core tablet weight | 600 |
| Stage-D: (Coating) | |
| Opadry II ® 85F520152 yellow | 18 |
| Water, purified | q.s. |
| Coated tablet weight | 618 |

Process:

Posaconazole and the excipients of stage A were sifted and blended, and then subjected to hot melt extrusion. The extrudate was milled and coated with the material of stage B by top-spray granulation. Low-substituted hydroxypropyl cellulose, microcrystalline cellulose, silicon dioxide, croscarmellose sodium, and sodium stearylfumarate of stage C were sifted and blended with the enteric-coated extrudate. The mixture was subjected to compression to obtain a tablet, which was finally film-coated.

Example 3

| Ingredients | mg |
|---|---|
| Stage-A: (Hot-melt extrusion) | |
| Posaconazole (Form I) | 100 |
| Methacrylic acid/ethyl acrylate copolymer (1:1), Type B (Kollicoat ® MAE 100P) | 150 |
| Polyethylene glycol 4000 (Macrogol 4000) | 30 |
| Copovidone (Kollidon ® VA 64) | 25 |
| Total weight after HME | 305 |
| Stage-B: (Lubrication and compression) | |
| Posaconazole HME granules | 305 |
| Low-substituted Hydroxypropylcellulose (L-HPC LH-11) | 103 |
| Microcrystalline cellulose (Comprecel ® M 102D+) | 105.5 |
| Colloidal silicon dioxide (Aerosil ® 200 pharma) | 24 |
| Croscarmellose sodium | 60 |
| Magnesium Stearate | 2.5 |
| Core tablet weight | 600 |
| Stage-C: (Film Coating) | |
| Opadry ® II 85F520152 yellow | 18 |
| Water, purified | q.s. |
| Coated tablet weight | 618 |

Process:

Posaconazole and the excipients of stage A were sifted and blended. The mixture was subjected to hot melt extrusion and the obtained extrudate was milled. Low-substituted hydroxypropylcellulose, microcrystalline cellulose, silicon dioxide, croscarmellose sodium, and magnesium stearate of stage B were sifted and blended with the extrudate. The mixture was subjected to compression to obtain a tablet, which was finally film-coated.

Example 4

| Ingredients | mg |
|---|---|
| Stage-A: (Hot-melt extrusion) | |
| Posaconazole (Form I) | 100 |
| Methacrylic acid/ethyl acrylate copolymer (1:1), Type B (Kollicoat ® MAE 100P) | 162 |
| Polyethylene glycol (Macrogol 1450) | 30 |
| Copovidone (Kollidon ® VA 64) | 50 |
| Xylitol (Xylisorb ® 90) | 20 |
| Total weight after HME | 362 |
| Stage-B: (Lubrication and compression) | |
| Posaconazole HME granules | 362 |
| Low-substituted Hydroxypropylcellulose (L-HPC LH-11) | 60 |
| Microcrystalline cellulose (Comprecel ® M 102D+) | 128 |
| Colloidal silicon dioxide (Aerosil ® 200 pharma) | 4 |
| Croscarmellose sodium | 42 |

-continued

| Ingredients | mg |
|---|---|
| Stage-C: (Lubrication) | |
| Sodium stearyl fumarate (Pruv ®) | 4 |
| Core tablet weight | 600 |
| Stage-D: (Film Coating) | |
| Opadry ® II 85F520152 yellow | 18 |
| Water, purified | q.s. |
| Coated tablet weight | 618 |

Process:

Posaconazole and the excipients of stage A were sifted and blended. The mixture was subjected to hot melt extrusion and the obtained extrudate was milled. Low-substituted hydroxypropylcellulose, microcrystalline cellulose, silicon dioxide, and croscarmellose sodium of stage B were sifted and blended with the extrudate. The mixture was lubricated with sodium stearyl fumarate and then subjected to compression to obtain a tablet, which was finally film-coated.

Example 5

| Ingredients | mg |
|---|---|
| Stage-A: (Hot-melt extrusion) | |
| Posaconazole (Form I) | 100 |
| Methacrylic acid/ethyl acrylate copolymer (1:1), Type B (Kollicoat ® MAE 100P) | 162 |
| Polyethylene glycol (Carbowax ™ Sentry ™) | 30 |
| Copovidone (Kollidon ® VA 64) | 50 |
| Xylitol (Xylisorb ® 90) | 20 |
| Total weight after HME | 362 |
| Stage-B: (Lubrication and compression) | |
| Posaconazole HME granules | 362 |
| Hydroxypropyl cellulose (Klucel EXF Pharma) | 75 |
| Microcrystalline cellulose (Comprecel ® M 102D+) | 113 |
| Colloidal silicon dioxide (Aerosil ® 200 pharma) | 4 |
| Croscarmellose sodium | 42 |
| Stage-C: (Lubrication) | |
| Sodium stearyl fumarate (Pruv ®) | 4 |
| Core tablet weight | 600 |
| Stage-D: (Film Coating) | |
| Opadry ® II 85F520152 yellow | 18 |
| Water, purified | q.s. |
| Coated tablet weight | 618 |

Process:

Posaconazole and the excipients of stage A were sifted and blended. The mixture was subjected to hot melt extrusion and the obtained extrudate was milled. Hydroxypropyl cellulose, microcrystalline cellulose, silicon dioxide, and croscarmellose sodium of stage B were sifted and blended with the extrudate. The mixture was lubricated with sodium stearyl fumarate and then subjected to compression to obtain a tablet, which was finally film-coated.

Example 6

| Ingredients | mg |
|---|---|
| Stage-A: (Hot-melt extrusion) | |
| Posaconazole (Form I) | 100 |
| Methacrylic acid/ethyl acrylate copolymer (1:1), Type B (Kollicoat ® MAE 100P) | 162 |
| Polyethylene glycol (Carbowax ™ Sentry ™) | 30 |
| Copovidone (Kollidon ® VA 64) | 50 |
| Xylitol (Xylisorb ® 90) | 20 |
| Propyl gallate | 2 |
| Total weight after HME | 364 |
| Stage-B: (Lubrication and compression) | |
| Posaconazole HME granules | 364 |
| Hydroxypropyl cellulose (Klucel EXF Pharma) | 75 |
| Microcrystalline cellulose (Comprecel ® M 102D+) | 111 |
| Colloidal silicon dioxide (Aerosil ® 200 pharma) | 4 |
| Croscarmellose sodium | 42 |
| Stage-C: (Lubrication) | |
| Sodium stearyl fumarate (Pruv ®) | 4 |
| Core tablet weight | 600 |
| Stage-D: (Film Coating) | |
| Opadry ® II 85F520152 yellow | 18 |
| Water, purified | q.s. |
| Coated tablet weight | 618 |

Process:

Posaconazole and the excipients of stage A were sifted and blended. The mixture was subjected to hot melt extrusion and the obtained extrudate was milled. Hydroxypropyl cellulose, microcrystalline cellulose, silicon dioxide, and croscarmellose sodium of stage B were sifted and blended with the extrudate. The mixture was lubricated with sodium stearyl fumarate and then subjected to compression to obtain a tablet, which was finally film-coated.

Examples 7a and 7b

| Ingredients | Ex. 7a mg | Ex. 7b mg |
|---|---|---|
| Stage-A: (Granulation) | | |
| Methacrylic acid/ethyl acrylate copolymer (1:1), Type B (Kollicoat ® MAE 100P) | 162 | 162 |
| Copovidone (Kollidon ® VA 64) | 50 | 50 |
| Triethyl citrate | 30 | 30 |
| Total weight after granulation | 242 | 242 |
| Stage-B: (Hot-melt extrusion) | | |
| Granules | 242 | 242 |
| Posaconazole (Form I) | 100 | — |
| Posaconazole (amorphous) | — | 100 |
| Xylitol (Xylisorb ® 90) | 20 | 20 |
| Propyl gallate | 2 | 2 |
| Total weight after HME | 364 | 364 |
| Stage-C: (Blending) | | |
| Posaconazole HME granules | 364 | 364 |
| Hydroxypropyl cellulose (Klucel EXF Pharma) | 75 | 75 |
| Microcrystalline cellulose (Comprecel ® M 102D+) | 111 | 111 |
| Colloidal silicon dioxide (Aerosil ® 200 pharma) | 4 | 4 |
| Croscarmellose sodium | 42 | 42 |

-continued

| Ingredients | Ex. 7a mg | Ex. 7b mg |
|---|---|---|
| Stage-D: (Lubrication) | | |
| Sodium stearyl fumarate (Pruv ®) | 4 | 4 |
| Core tablet weight | 600 | 600 |
| Stage-E: (Film Coating) | | |
| Opadry ® II 85F520152 yellow | 18 | 18 |
| Water, purified | q.s. | q.s. |
| Coated tablet weight | 618 | 618 |

Process:

The excipients of stage A were sifted and granulated. Posaconazole and the excipients of stage B were sifted and blended with the granules of stage A. The mixture was subjected to hot melt extrusion and the obtained extrudate was milled. Hydroxypropyl cellulose, microcrystalline cellulose, silicon dioxide, and croscarmellose sodium of stage C were sifted and blended with the extrudate. The mixture was lubricated with sodium stearyl fumarate and then subjected to compression to obtain a tablet, which was finally film-coated.

Example 8

| Ingredients | mg |
|---|---|
| Stage-A: (Granulation) | |
| Methacrylic acid/ethyl acrylate copolymer (1:1), Type B (Kollicoat ® MAE 100P) | 162 |
| Triethyl citrate | 30 |
| Total weight after granulation | 192 |
| Stage-B: (Hot-melt extrusion) | |
| Granules | 192 |
| Posaconazole (Form I) | 100 |
| Povidone K 30 | 25 |
| Xylitol (Xylisorb ® 90) | 40 |
| Propyl gallate | 2 |
| Total weight after HME | 359 |
| Stage-C: (Blending) | |
| Posaconazole HME granules | 359 |
| Hydroxypropyl cellulose (Klucel EXF Pharma) | 75 |
| Microcrystalline cellulose (Comprecel ® M 102D+) | 116 |
| Colloidal silicon dioxide (Aerosil ® 200 pharma) | 4 |
| Croscarmellose sodium | 42 |
| Stage-D: (Lubrication) | |
| Sodium stearyl fumarate (Pruv ®) | 4 |
| Core tablet weight | 600 |
| Stage-E: (Film Coating) | |
| Opadry ® II 85F520152 yellow | 18 |
| Water, purified | q.s. |
| Coated tablet weight | 618 |

Process:

The excipients of stage A were sifted and granulated. Posaconazole and the excipients of stage B were sifted and blended with the granules of stage A. The mixture was subjected to hot melt extrusion and the obtained extrudate was milled. Hydroxypropyl cellulose, microcrystalline cellulose, silicon dioxide, and croscarmellose sodium of stage C were sifted and blended with the extrudate. The mixture was lubricated with sodium stearyl fumarate and then subjected to compression to obtain a tablet, which was finally film-coated.

Examples 9a and 9b

| Ingredients | Ex. 9a mg | Ex. 9b mg |
|---|---|---|
| Stage-A: (Granulation) | | |
| Methacrylic acid/ethyl acrylate copolymer (1:1), Type B (Kollicoat ® MAE 100P) | 250 | 250 |
| Triethyl citrate | 30 | 10 |
| Total weight after granulation | 280 | 260 |
| Stage-B: (Hot-melt extrusion) | | |
| Granules | 280 | 260 |
| Posaconazole (Form I) | 100 | 100 |
| Hydroxypropyl cellulose (Klucel EXF Pharma) | 75 | 75 |
| Xylitol (Xylisorb ® 90) | 28 | 28 |
| Propyl gallate | 2 | 1 |
| Total weight after HME | 485 | 464 |
| Stage-C: (Blending) | | |
| Posaconazole HME granules | 485 | 464 |
| Hydroxypropyl cellulose (Klucel EXF Pharma) | 30 | 30 |
| Microcrystalline cellulose | 180 | 64 |
| Colloidal silicon dioxide (Aerosil ® 200 pharma) | 3 | 3 |
| Croscarmellose sodium | 35 | 35 |
| Stage-D: (Lubrication) | | |
| Sodium stearyl fumarate (Pruv ®) | 4 | 4 |
| Core tablet weight | 737 | 600 |
| Stage-E: (Film Coating) | | |
| Opadry ® II 85F520152 yellow | 22 | 24 |
| Water, purified | q.s. | q.s. |
| Coated tablet weight | 759 | 624 |

Process:

The excipients of stage A were sifted and granulated. Posaconazole and the excipients of stage B were sifted and blended with the granules of stage A. The mixture was subjected to hot melt extrusion and the obtained extrudate was milled. Hydroxypropyl cellulose, microcrystalline cellulose, silicon dioxide, and croscarmellose sodium of stage C were sifted and blended with the extrudate. The mixture was lubricated with sodium stearyl fumarate and then subjected to compression to obtain a tablet, which was finally film-coated.

Examples 10a and 10b

| Ingredients | Ex. 10a mg | Ex. 10b mg |
|---|---|---|
| Stage-A: (Hot-melt extrusion) | | |
| Posaconazole (Form I) | 100 | 100 |
| Methacrylic acid/ethyl acrylate copolymer (1:1), Type B (Kollicoat ® MAE 100P) | 162 | 162 |

| Ingredients | Ex. 10a mg | Ex. 10b mg |
|---|---|---|
| Polyethylene glycol (Carbowax ™ Sentry ™) | 30 | 30 |
| Copovidone (Kollidon ® VA 64) | 50 | 50 |
| Xylitol (Xylisorb ® 90) | 20 | 20 |
| Total weight after HME | 362 | 362 |
| Stage-B: (Lubrication and compression) | | |
| Posaconazole HME granules | 362 | 362 |
| Hydroxypropyl cellulose (Klucel ELF Pharma) | 125 | 125 |
| Microcrystalline cellulose (Comprecel ® M 102D+) | 63 | 63 |
| Colloidal silicon dioxide (Aerosil ® 200 pharma) | 4 | 4 |
| Croscarmellose sodium | 42 | 42 |
| Propyl gallate | — | 0.65 |
| Stage-C: (Lubrication) | | |
| Sodium stearyl fumarate (Pruv ®) | 4 | 4 |
| Core tablet weight | 600 | 600.65 |
| Stage-D: (Film Coating) | | |
| Opadry ® II 85F520152 yellow | 18 | 18 |
| Water, purified | q.s. | q.s. |
| Coated tablet weight | 618 | 618.65 |

Process:

Posaconazole and the excipients of stage A were sifted and blended. The mixture was subjected to hot melt extrusion and the obtained extrudate was milled. Hydroxypropyl cellulose, microcrystalline cellulose, silicon dioxide, croscarmellose sodium and optionally propyl gallate of stage B were sifted and blended with the extrudate. The mixture was lubricated with sodium stearyl fumarate and then subjected to compression to obtain a tablet, which was finally film-coated.

Example 11

| Ingredients | mg |
|---|---|
| Stage-A: (Granulation) | |
| Methacrylic acid/ethyl acrylate copolymer (1:1), Type B (Kollicoat ® MAE 100P) | 162 |
| Copovidone (Kollidon ® VA 64) | 50 |
| Triethyl citrate | 30 |
| Total weight after granulation | 242 |
| Stage-B: (Hot-melt extrusion) | |
| Granules | 242 |
| Posaconazole (Form I) | 100 |
| Xylitol (Xylisorb ® 90) | 20 |
| Propyl gallate | 2 |
| Total weight after HME | 364 |
| Stage-C: (Blending) | |
| Posaconazole HME granules | 364 |
| Hydroxypropyl cellulose (Klucel EXF Pharma) | 75 |
| Microcrystalline cellulose (Comprecel ® M 102D+) | 111 |
| Colloidal silicon dioxide (Aerosil ® 200 pharma) | 4 |
| Croscarmellose sodium | 42 |
| Stage-D: (Lubrication) | |
| Sodium stearyl fumarate (Pruv ®) | 4 |
| Core tablet weight | 600 |
| Stage-E: (Film Coating) | |
| Opadry ® II 85F520152 yellow | 18 |
| Water, purified | q.s. |
| Coated tablet weight | 618 |

Process:

The excipients of stage A were sifted and granulated. Posaconazole and the excipients of stage B were sifted and blended with the granules of stage A. The mixture was subjected to hot melt extrusion and the obtained extrudate was milled. Hydroxypropyl cellulose, microcrystalline cellulose, silicon dioxide, and croscarmellose sodium of stage C were sifted and blended with the extrudate. The mixture was lubricated with sodium stearyl fumarate and then subjected to compression to obtain a tablet, which was finally film-coated.

Example 12

| Ingredients | mg |
|---|---|
| Stage-A: (Hot-melt extrusion) | |
| Posaconazole (Form I) | 100 |
| Methacrylic acid/ethyl acrylate copolymer (1:1), Type B (Kollicoat ® MAE 100P) | 250 |
| Hydroxypropyl cellulose (Klucel EXF Pharma) | 75 |
| Xylitol (Xylisorb ® 90) | 58 |
| Propyl gallate | 2 |
| Total weight after HME | 485 |
| Stage-B: (Blending) | |
| Microcrystalline cellulose (Comprecel ® M 102D+) | 73 |
| Colloidal silicon dioxide (Aerosil ® 200 pharma) | 3 |
| Croscarmellose sodium | 35 |
| Sodium stearyl fumarate (Pruv ®) | 4 |
| Core tablet weight | 600 |
| Stage-C: (Film Coating) | |
| Opadry ® II 85F520152 Yellow | 24 |
| Water, purified | q.s. |
| Coated tablet weight | 624 |

Process:

Posaconazole and the excipients of stage A were sifted and blended. The mixture was subjected to hot melt extrusion and the obtained extrudate was milled. Microcrystalline cellulose, silicon dioxide, croscarmellose sodium, and sodium stearyl fumarate were sifted and blended with the extrudate. The mixture was subjected to compression to obtain a tablet, which was finally film-coated.

Example 13—Stability Tests

Stability testing was conducted according to guideline Q 1 A (R2) of International Conference on Harmonization (ICH). The film-coated tablets were stored either for 48 hours at 80° C. and 40% relative humidity (80° C./40% RH) or for 3 and 6 months at accelerated conditions (40° C. and 75% relative humidity, 40° C./75% RH). The film-coated tablets stored for 48 hours at 80° C. and 40% RH were not packed, whereas the film-coated tablets tested under accelerated conditions (40° C./75% RH for 3 and 6 months) were packed in alu-alu blisters.

TABLE 1

| Sample | Total impurities (%) | |
| --- | --- | --- |
| | Initial | 48 hr at 80° C./40% RH |
| Example 10a | 0.51 | 1.43 |
| Example 10b | 0.46 | 1.26 |
| Example 6 | 0.11 | 0.28 |
| Example 11 | 0.19 | 0.39 |

TABLE 2

| Sample | Total impurities (%) | | |
| --- | --- | --- | --- |
| | Initial | 3 months at 40° C./75% RH | 6 M at 40° C./75% RH |
| Example 10a | 0.51 | — | 1.02 |
| Example 10b | 0.46 | — | 1.07 |
| Example 6 | 0.11 | — | — |
| Example 11 | 0.19 | 0.16 | 0.41 |

Example 14a-g

Stability testing was conducted according to guideline Q 1 A (R2) of International Conference on Harmonization (ICH). The granulate was stored either for 48 hours at 80° C. and 40% relative humidity (80° C./40% RH) or for 3 months at accelerated conditions (40° C. and 75% relative humidity, 40° C./75% RH).

| Ingredients | Ex. 14a mg | Ex. 14b mg | Ex. 14c mg | Ex. 14d mg | Ex. 14e mg | Ex. 14f mg | Ex. 14g mg |
| --- | --- | --- | --- | --- | --- | --- | --- |
| Hot-melt extrusion | | | | | | | |
| Posaconazole (Form-I) | 100 | 100 | 100 | 100 | 100 | 100 | 100 |
| Kollicoat ® MAE 100P | 162 | 162 | 162 | 162 | 162 | 162 | 162 |
| Povidone K 30 (Plasdone ® K 29/32) | — | — | 25 | 25 | 25 | 25 | 25 |
| Polyethylene glycol (PEG 1450) | 50 | 50 | 30 | 30 | 30 | 30 | 50 |
| Propyl gallate | — | 2 | — | — | 2 | — | — |
| Butyl hydroxy toluene (BHT) | 0.13 | — | — | 0.13 | — | — | — |
| Sodium metabisulfite | — | — | — | — | — | 2.5 | — |
| Kolliphor ® TPGS | — | — | — | — | — | — | 1 |
| Total weight | 312.13 | 314 | 317 | 317.13 | 319 | 319.5 | 338 |
| Total impurities (%) | | | | | | | |
| Initial | 0.45 | 0.18 | 0.39 | 0.49 | 0.25 | 0.29 | 0.24 |
| 80° C./40% RH - 48 h (open) | 0.80 | 0.24 | 1.74 | 1.27 | 0.24 | 1.46 | 1.13 |
| 40° C./75% RH - 3 M (open) | 0.68 | 0.32 | 1.31 | 0.85 | 0.34 | 0.54 | 0.79 |

Process:

Posaconazole and the excipients were sifted and blended. The mixture was subjected to hot melt extrusion and the obtained extrudate was milled. The granules were subjected to the stability testing.

The invention claimed is:

1. A gastro-resistant pharmaceutical composition comprising posaconazole, wherein the posaconazole is molecularly dispersed in a mixture containing an enteric polymer and a non-enteric polymer, the mixture is prepared by hot-melt extrusion, wherein the enteric polymer and non-enteric polymer are present in a ratio of 6:1 to 1:1 and the gastro-resistant pharmaceutical composition releases posaconazole in the intestine and releases ≤10% of the posaconazole in 0.1M HCl after two hours.

2. The composition according to claim 1, wherein the enteric polymer is selected from hypromellose derivatives, cellulose derivatives, polyvinylacetate derivatives and polymethacrylic acid derivatives.

3. The composition according to claim 2, wherein the enteric polymer is a polymethacrylic acid derivative selected from poly(methacrylic acid/methyl methacrylate) and poly(methacrylic acid/ethyl acrylate).

4. The composition according to claim 2, wherein the non-enteric polymer is selected from polyvinylpyrrolidone, poly(vinylpyrrolidone/vinylacetate), polyvinylcaprolactam/polyvinylacetate/polyethylene glycol graft copolymer, polyethylene glycol/polyvinyl alcohol graft copolymer, poly(ethylene oxide/propylene oxide), macrogolglycerol hydroxystearate, polyethylene glycol, hypromellose, hydroxypropyl cellulose, hydroxyethyl cellulose and maltodextrins.

5. The composition according to claim 2, wherein the composition contains an antioxidant.

6. The composition according to claim 3, wherein the non-enteric polymer is selected from polyvinylpyrrolidone, poly(vinylpyrrolidone/vinylacetate), polyvinylcaprolactam/polyvinylacetate/polyethylene glycol graft copolymer, polyethylene glycol/polyvinyl alcohol graft copolymer, poly(ethylene oxide/propylene oxide), macrogolglycerol hydroxystearate, polyethylene glycol, hypromellose, hydroxypropyl cellulose, hydroxyethyl cellulose and maltodextrins.

7. The composition according to claim 3, wherein the composition contains an antioxidant.

8. The composition according to claim 1, wherein the non-enteric polymer is selected from polyvinylpyrrolidone, poly(vinylpyrrolidone/vinylacetate), polyvinylcaprolactam/polyvinylacetate/polyethylene glycol graft copolymer, polyethylene glycol/polyvinyl alcohol graft copolymer, poly(ethylene oxide/propylene oxide), macrogolglycerol hydroxystearate, polyethylene glycol, hypromellose, hydroxypropyl cellulose, hydroxyethyl cellulose and maltodextrins.

9. The composition according to claim 8, wherein the enteric polymer is poly(methacrylic acid/ethyl acrylate) and the non-enteric polymer is selected from poly(vinyl-pyrrolidone/vinylacetate), polyethylene glycol, hydroxypropyl cellulose and polyvinylpyrrolidone.

10. The composition according to claim 8, wherein the composition contains an antioxidant.

11. The composition according to claim 1, wherein the composition contains an antioxidant.

12. The composition according to claim 11, wherein the antioxidant is contained in the mixture.

13. The composition according to claim 11, wherein the antioxidant is selected from butylated hydroxytoluene (BHT), butylated hydroxyanisole (BHA), sodium metabisulfite or potassium metabisulfite, sodium bisulfite, sodium sulfite, sodium thiosulfate, cysteine, acetyl cysteine, methionine, glutathione, sodium formaldehyde sulfoxylate, ascorbic acid and ascorbic derivatives, ascorbyl palmitate, tocopherol and tocopherol derivatives, tocopheryl succinate, tocopheryl polyethylene glycol succinate (TPGS) and propyl gallate.

14. The composition according to claim 1, wherein the mixture contains a monomeric plasticizer.

15. The composition according to claim 14, wherein the monomeric plasticizer is selected from triethyl citrate, triacetin, dibutyl sebacate, diethyl phthalate, glycerylmonostearate, glycerine and propylene glycol.

16. The composition according to claim 1, wherein the mixture contains a sugar alcohol.

17. The composition according to claim 16, wherein the sugar alcohol is selected from xylitol, sorbitol, mannitol and maltitol.

18. The composition according to claim 1, wherein the composition is a granulate material.

19. The composition according to claim 18, wherein the granules are coated with an enteric polymer.

20. The composition according to claim 19, wherein the enteric coating of the granules and the enteric polymer constituent of the granules comprise the same enteric polymer.

21. The composition according to claim 18, wherein the granules are filled into a capsule or compressed into a tablet.

* * * * *